United States Patent [19]

Lewis

[11] 4,141,686
[45] Feb. 27, 1979

[54] DISPOSABLE LIQUID STERILIZER UNIT

[76] Inventor: James H. Lewis, P.O. Box 2341, London, Canada

[21] Appl. No.: 781,021

[22] Filed: Mar. 24, 1977

[51] Int. Cl.² ............................. C02B 1/00; C02B 3/02
[52] U.S. Cl. ..................................... 250/436; 250/438;
250/436; 422/24
[58] Field of Search ....................... 21/102 R, DIG. 2;
250/436, 438, 455; 210/243

[56] References Cited

U.S. PATENT DOCUMENTS

| | | | |
|---|---|---|---|
| 1,670,217 | 5/1928 | Scheidt | 21/DIG. 2 |
| 3,562,520 | 2/1971 | Hippen | 21/102 R |
| 3,791,790 | 2/1974 | Wyndham et al. | 21/102 R |
| 3,825,494 | 7/1974 | Call et al. | 21/102 R |
| 3,948,772 | 4/1976 | Elwer | 21/102 R |
| 4,008,045 | 2/1977 | Free | 21/102 R |

FOREIGN PATENT DOCUMENTS

| | | | |
|---|---|---|---|
| 357083 | 4/1936 | Canada | 250/436 |
| 498015 | 12/1953 | Canada. | |
| 501434 | 4/1954 | Canada. | |
| 610989 | 12/1960 | Canada. | |
| 674555 | 11/1963 | Canada. | |
| 712304 | 6/1965 | Canada. | |
| 739145 | 7/1966 | Canada | 250/436 |
| 767856 | 9/1967 | Canada. | |
| 841135 | 5/1970 | Canada. | |
| 1295774 | 5/1962 | France | 21/102 R |

*Primary Examiner*—Morris O. Wolk
*Assistant Examiner*—Bradley Garris
*Attorney, Agent, or Firm*—Townsend and Townsend

[57] ABSTRACT

A disposable liquid sterilizer unit incorporating an ultraviolet tube designed to generate radiation at approximately 2537 Angstroms. The unit comprises an elongated cylindrical plastic jacket opaque to ultra-violet radiation concentrically mounted about the tube to provide a chamber between the jacket and the tube for the flow of liquid to be exposed to radiation generated by the tube. The tube extends beyond the ends of the jacket and includes electrical connectors at each end for removably mounting the unit to make electrical connection with electrical connections in a casing. A seal is provided adjacent each end of the jacket against liquid flow from the chamber between the tube and the walls of the jacket to the exterior of the jacket. Inlet and outlet connections for the flow of water to and from the chamber are provided as well as a viewport through the plastic jacket. The jacket includes a central portion and two integral injection moulded end portions fixed to the central portion by an adhesive. The moulded end portions include the inlet and outlet connections. The complete unit can be readily removed from the casing and disposed of when the tube is defective or worn out. One circuit arangement provides a visual warning, while another prevents the flow of liquid past the tube when insufficient current to achieve sterilization is flowing through the tube.

13 Claims, 16 Drawing Figures

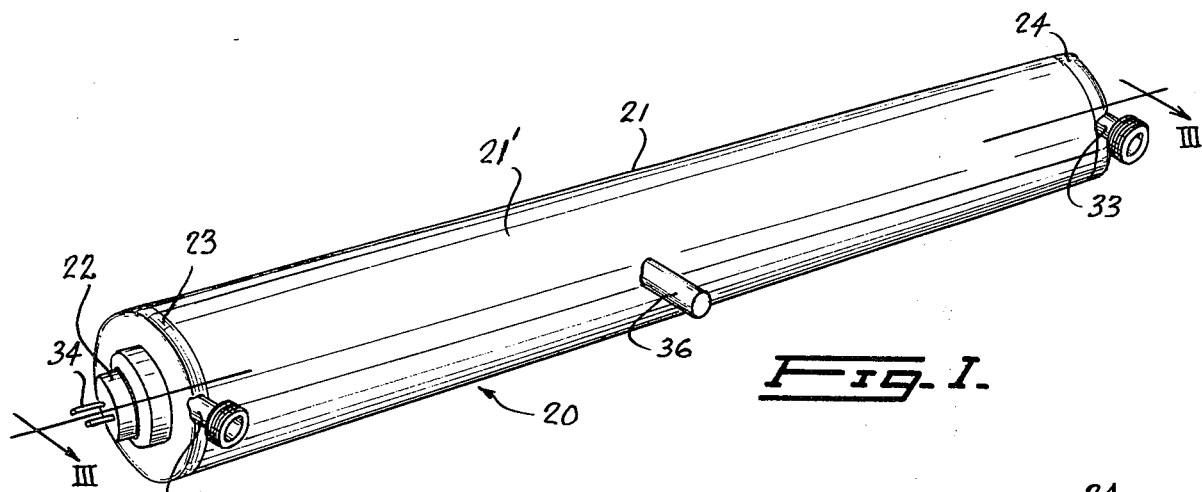
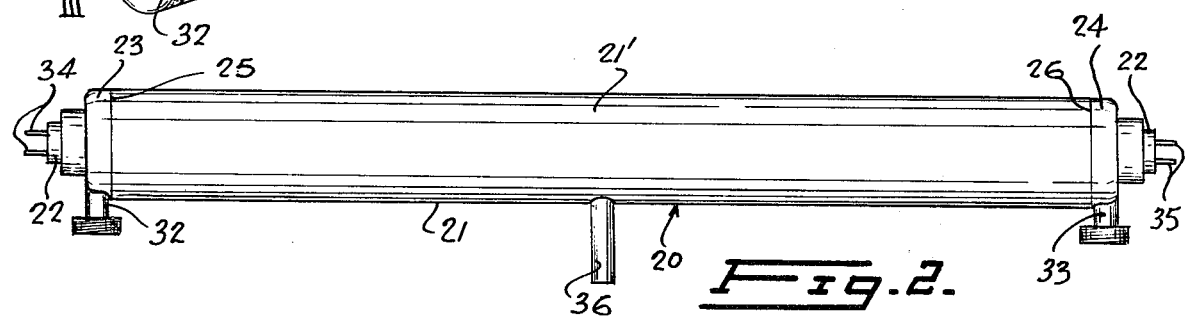
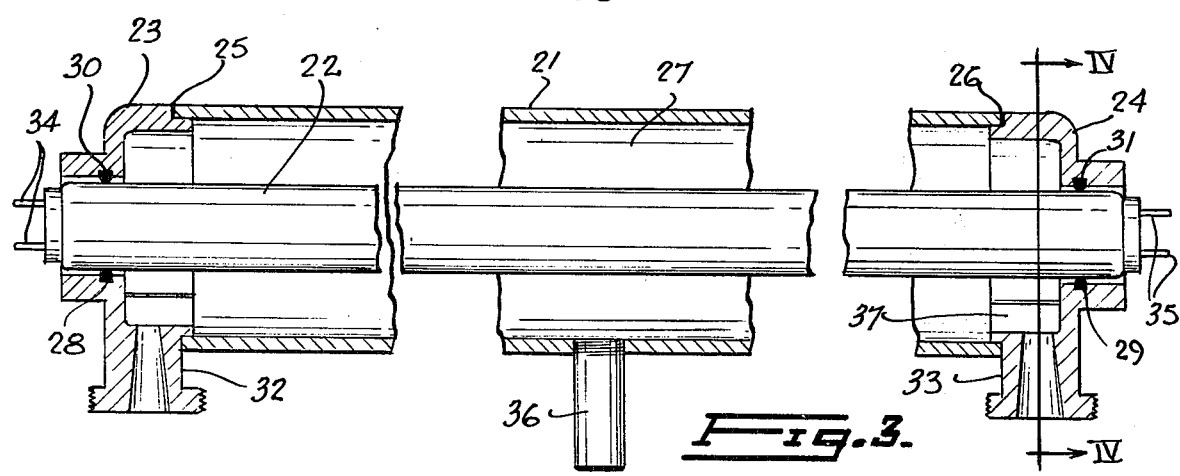
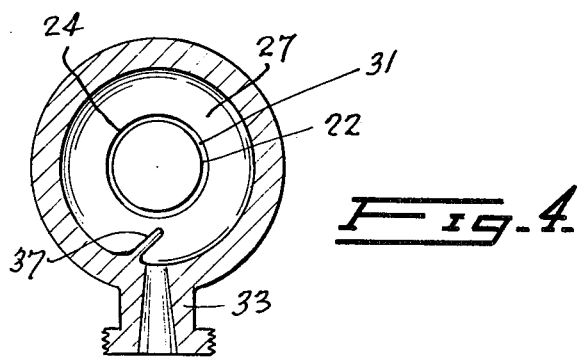

74 To A.C. SOURCE

DISPOSABLE LIQUID STERILIZER UNIT

BACKGROUND OF THE INVENTION

This invention relates to liquid sterilizers and more particularly to water sterilizers employing ultra-violet radiation to kill bacteria.

It is well known to sterilize water by exposing the water to ultra-violet radiation at a wavelength of approximately 2537 Angstroms. In a typical sterilizer, water is exposed to ultra-violet radiation as it is introduced through an inlet into a cylinder housing an ultra-violet tube, the water then flowing through the length of the cylinder where it exits through an outlet. The water is sterilized as it is exposed to the ultra-violet radiation generated by the tube.

It is also known to sterilize water by exposing the water to ozone generated at a wavelength of approximately 1880 Angstroms. The ozone can be generated by means of a tube of similar construction to that of an ultra-violet radiation generator, or by means of an electrical arc generated in the water. The known ozone generator leaves a residue of ozone in the water, which continues to sterilize the water as it passes through the cylinder.

It is also possible to sterilize water utilizing gamma ray radiation. Thus, the principles of this invention apply to all of these known kinds of sterilizers. However, the invention will be specifically described with reference to embodiments employing ultra-violet radiation.

Although sterilization of water by use of ultra-violet radiation has an excellent reputation for killing bacteria, such sterilizers have tended to be expensive, and also require specialized skills for installation and maintenance. However, there is a need for a water sterilizer that a home or cottage owner can afford and can install and maintain without having specialized skills.

One of the problems associated with known sterilizers, which contributes to their complexity, is that they are designed as permanent installations, except for the replacement of worn out or defective bulbs. As a consequence, these sterilizers have complex mounting arrangements for the tube, the end seal connections and the water inlet and outlet. Also, because the known sterilizers were designed as permanent installations, the water supply connections tended to be complex, again requiring specialized skills for installation. Since the tubes are also quite delicate, there is a serious risk of tubes being broken on replacement, if done by anyone other than a trained technician.

An example of a prior art sterilizer of complex design is described in Canadian Pat. No. 610,989, which issued to Corn Products Company on Dec. 20, 1960. This patented sterilizer was clearly designed as a permanent installation except for replacement of the ultra-violet tubes. For example, the inlet and outlet ports are formed of conduits, nipples, adapters, gaskets and screws. The ends of the ultra-violet tubes are connected to electrical sockets that are mounted on connector blocks slidably mounted on connector block plates and locked in place. When a tube is to be replaced, these connectors have to be removed from the connector blockplates. It can be readily appreciated that specialized skills are thus required both for initial installation and maintenance. Resealing of the sterilizer when replacing a lamp also poses a problem.

As is well known, ultra-violet tubes operate more efficiently at higher temperatures. One known type of water sterilizer, therefore, provides a protective quartz sheath surrounding the tube, thereby leaving an air space between the sheath and the tube to provide insulation for the tube from the water flowing around the sheath. However, such sheaths suffer from the disadvantage of having to be cleaned periodically to remove collected dust, which can inhibit the penetration of light from the tube through the sheath to the water, resulting in reduced efficiency and risk of non-sterilization. Thus, the cleaning of the sheaths has to be done by a skilled technician. Special handling is also required, especially because the quartz is susceptible to finger prints, and because the quality of quartz required produces a fragile sheath that can be broken very easily. From the above discussion, it can be appreciated that prior art water sterilizers employing sheaths are expensive and require specialized skills for their installation and maintenance. Canadian Pat. No. 610,989 employes such a quartz sheath, adding to the complexity, fragility and cost of the sterilizer.

Other known prior art sterilizers employ sensing devices to sense the amount of light radiated by the ultra-violet tube, coupled with an electro-magnetic control device to control valves at the water inlet. Thus, if the tube is not emitting sufficient light to sterilize, the valve at the inlet is closed and the unit fails safe. Although serving a useful purpose, such fail safe devices add to the expense of a sterilizer unit. A prior art sterilizer employing such a fail safe device is described in Canadian Pat. No. 674,555, which issued to Allsafe Water Sterilizer Ltd. on Nov. 19, 1963. The Allsafe sterilizer is another example of one employing a protective sheath and designed as a permanent installation except for replacement of lamps, again involving a complex mechanical end cap arrangement requiring specialized skills for maintenance.

Canadian Pat. No. 767,856 granted Sept. 26, 1967 and Canadian Pat. No. 841,135, granted May 5, 1970, and invented by James W. Harrison, are further examples of sterilizers that are designed to fail safe. The sterilizers described in these patents are of the permanent installation type requiring the removal of end caps for replacement of ultra-violet tubes.

SUMMARY OF THE INVENTION

The invention comprises a disposable sterilizer unit having a small inexpensive jacket and radiation generating tube which can be manufactured very inexpensively and which is designed to permit a person with no specialized skills to install it and dispose of it when the tube is defective or has worn out.

In the preferred embodiment of the invention, the protective quartz sheath found in many known sterilizer units is eliminated by allowing the radiation generating tube to be directly exposed to the water within the cylinder. This normally would reduce the capacity of the sterilizer to kill bacteria, due to lack of insulation and the resultant colder temperatures at the tube surface. However, this expected deficiency is offset by the provision of a tube having more output power, i.e. a tube twice as long as that normally required for standard water flow rates. Stated differently, instead of utilizing a sheath to compensate for inefficiencies of tubes at lower temperatures, the invention utilizes a more efficient tube, thereby permitting the sheath to be eliminated and avoiding its inherent problems outlined above. In the preferred embodiment, the water inlet and outlets are restricted in size to provide a maximum flow rate of only 4 gallons per minute. This flow rate provides an 8:1 safety factor for water at 2° C. It is to be understood, however, that the principles of this invention also apply to sterilizers incorporating sheaths.

According to one aspect of this invention, a disposable liquid sterilizer unit is provided comprising an elongated plastic jacket; means adapted to generate radiation to sterilize liquid when the liquid is exposed to radiation generated thereby; means for mounting the jacket about the generating means to define a chamber for the flow of liquid to be exposed to radiation generated by said generating means, the jacket being opaque to radiation generated by said generating means; means connected to the generating means and extending beyond the ends of the jacket for removably mounting the unit to make electrical connection with electrical connections in a casing; means adjacent each end of the jacket for providing a seal against liquid flow from the chamber to the exterior of the jacket; and means adjacent respective ends of the jacket to provide an inlet and an outlet connection for the flow of liquid to and from said chamber; the unit being adapted to be removed from the casing and disposed of when the tube is defective or worn out.

In the preferred embodiment of applicant's invention, the generating means is an ultra-violet tube designed to generate ultra-violet radiation at a wavelength of approximately 2537 Angstroms. An acrylic rod is threaded into the side of the jacket to be exposed to the light generated by the tube, and to thereby provide a viewport externally of the jacket for determining if the tube is operating. In another embodiment a circuit including an LED is provided for determining if the tube is operating.

Also in the preferred embodiment, the plastic jacket comprises a central portion and two end portions fixed thereto, each end portion comprising an integral injection molded part, including respective inlet and outlet connections. An O-ring is mounted in each end portion in annular grooves to provide a seal against water flow from the chamber to the exterior of the jacket.

Another embodiment provides a novel means for stopping the flow of liquid to the sterilizer unit when the tube fails to operate.

The preferred embodiment features the provision of simple end seal connections that reduce expense and facilitate installation; a simple mounting for the unit in its casing; and simple hose connections to the water inlet and outlet. In addition, there is no resealing problem on replacement since the disposable unit is factory sealed.

For a fuller understanding of the nature and advantages of the invention, reference should be had to the ensuing detailed description taken in conjunction with the accompanying drawings.

BRIEF DESCRIPTION OF THE DRAWINGS

FIG. 1 is a perspective view of a disposable water sterilizer unit;

FIG. 2 is a plan view of the same unit;

FIG. 3 is a horizontal sectional view of the unit taken along lines III—III of FIG. 1, showing the ultra-violet tube and the end sealing arrangements;

FIG. 4 is a sectional view taken along line IV—IV of FIG. 3 showing details of a water inlet or outlet connection;

DESCRIPTION OF THE PREFERRED EMBODIMENTS

Figure 5:
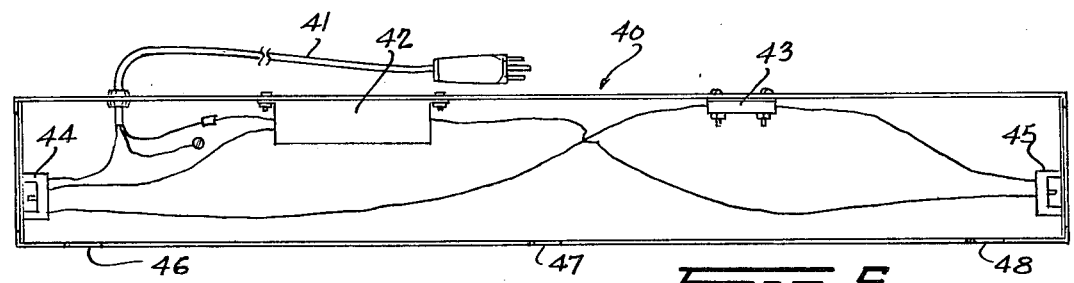
FIG. 5 is a plan view of a water sterilizer casing with the unit removed.

FIGS. 1 to 4 show an embodiment of a disposable water sterilizer unit 20, which essentially comprises an elongated cylindrical plastic jacket 21, typically made of ABS tubing, and an ultra-violet tube 22 designed to radiate light at a wavelength of approximately 2537 Angstroms to sterilize water exposed to the ultra-violet radiation.

The jacket 21 is composed of a central portion 21' and end portions 23 and 24. These end portions are injection molded parts and are fixed to the central portion 22 at 25 and 26 by means of a suitable adhesive. Of course, the jacket 21 can be formed of a single molded part.

As can be clearly seen from FIG. 3, the jacket 21 is cencentrically mounted about the tube 22 to provide a chamber 27 between the internal surface of the jacket and the external surface of the tube for the flow of water to be sterilized. The tube 22 passes through and beyond the end portions 23 and 24 of the jacket. The tube 22 is supported by the end portions 23 and 24 by means of a close fit between the extreme ends of reduced diameter and the surface of the tube, and by means of neoprene O-rings 28 and 29 located in grooves 30 and 31 of the end portions 23 and 24. These rings also provide a seal against water flow from the chamber 27 to the exterior of the jacket 21.

Water inlet and outlet connections 32 and 33 are also molded as part of the end portions 23 and 24 respectively, to provide connections to and from a water supply with access to the chamber 27.

Prongs 34 and 35 at the ends of the tube 22 serve as electrical connection means externally of the jacket to make electrical connection with electrical connections in a casing. An acrylic rod 36 is threaded into the wall of the jacket 21, and is exposed to the light generated from the tube 22 to provide a viewport for visually monitoring the operation of the tube. Acrylic has been chosen as the material for the rod, since it provides good stability in the presence of ultra-violet radiation.

As can best be seen in FIG. 4, the end portion 24 has molded therewith a fin 37, which imparts turbulence to the water flowing in and out of the jacket via the connections 32 and 33. It can also be seen that the connections 32 and 33 are threaded at their ends with a $\mu$ inch National Hose thread for easy connection to an ordinary automatic washing machine fill hose.

Turning now to FIGS. 5 to 9, an elongated, rectangular shape casing 40 is shown for incasing the disposable sterilizer unit 20. The casing has mounted thereon a standard electrical outlet 41, a standard ballast 42, a standard starter 43 and mounting receptacles 44 and 45 for the tube 22, together with their appropriate interconnected electrical wiring. The casing also includes three hemispherical notches 46, 47 and 48 in one side thereof.

Figure 6:
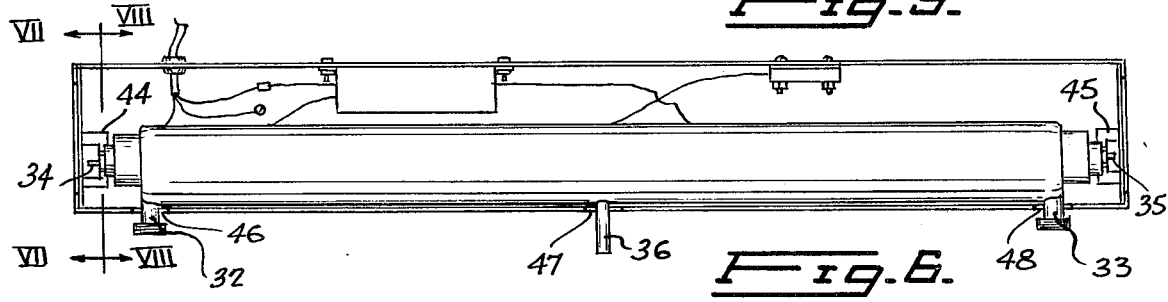
FIG. 6 is a similar view of the casing with the sterilizer unit installed.
Figure 7:
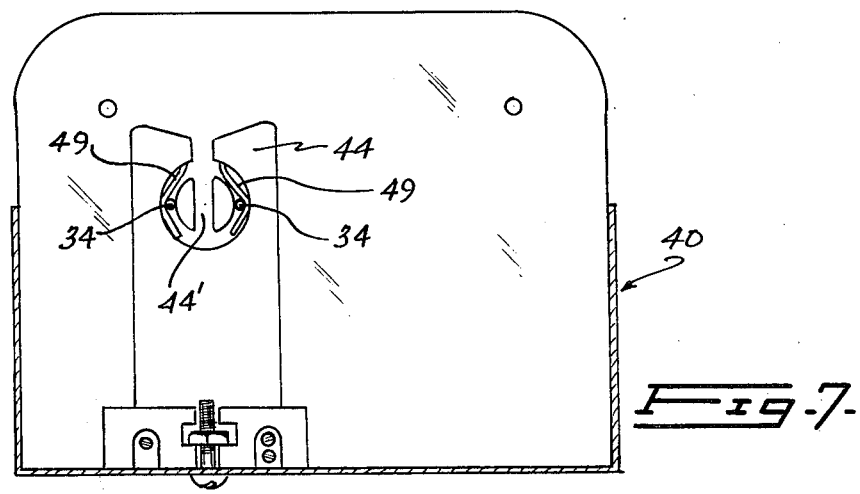
FIG. 7 is a view taken along line VII—VII of FIG. 6 showing details of the mounting receptacle in the casing.
Figure 8:
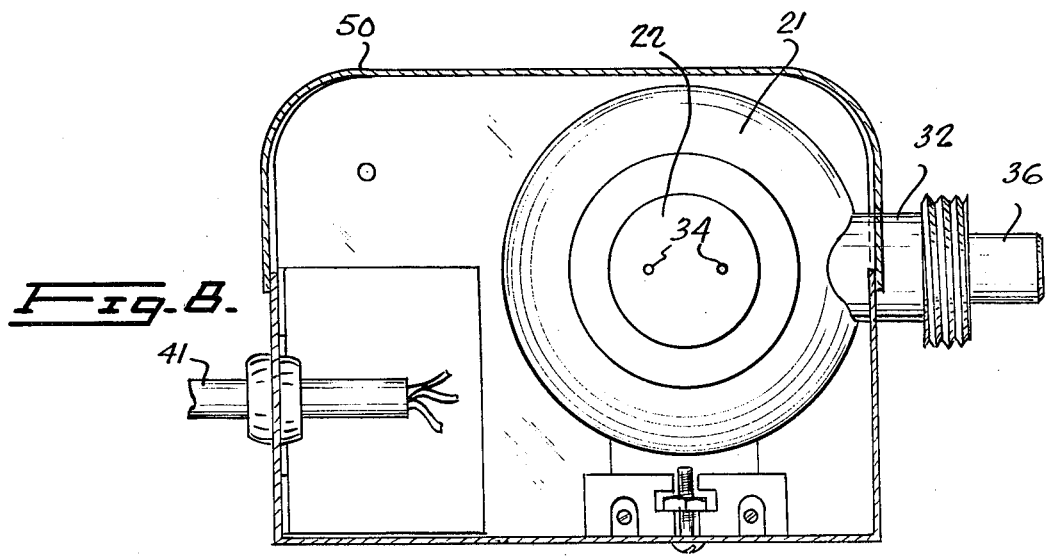
FIG. 8 is a view taken along line VIII—VIII of FIG. 6 showing more details.
Figure 9:
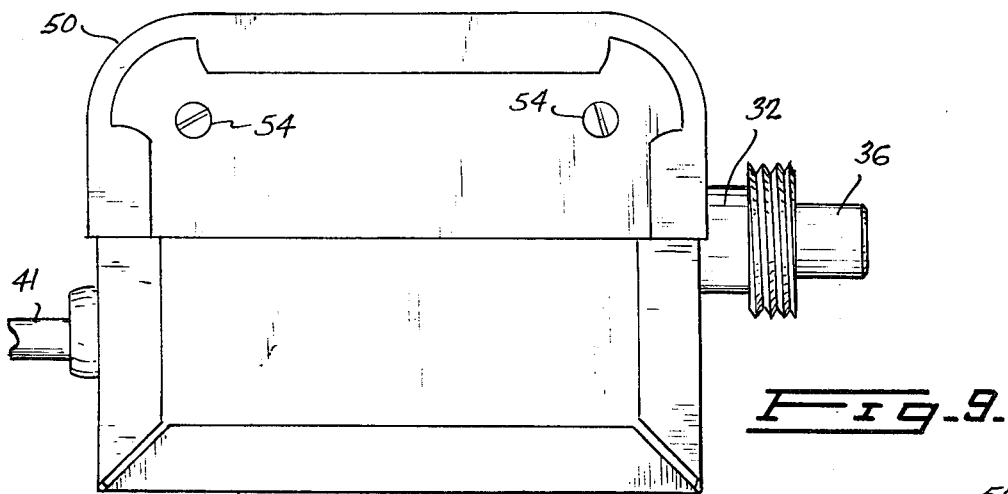
FIG. 9 is an end view of the casing with the cover mounted thereon.
Figure 10:
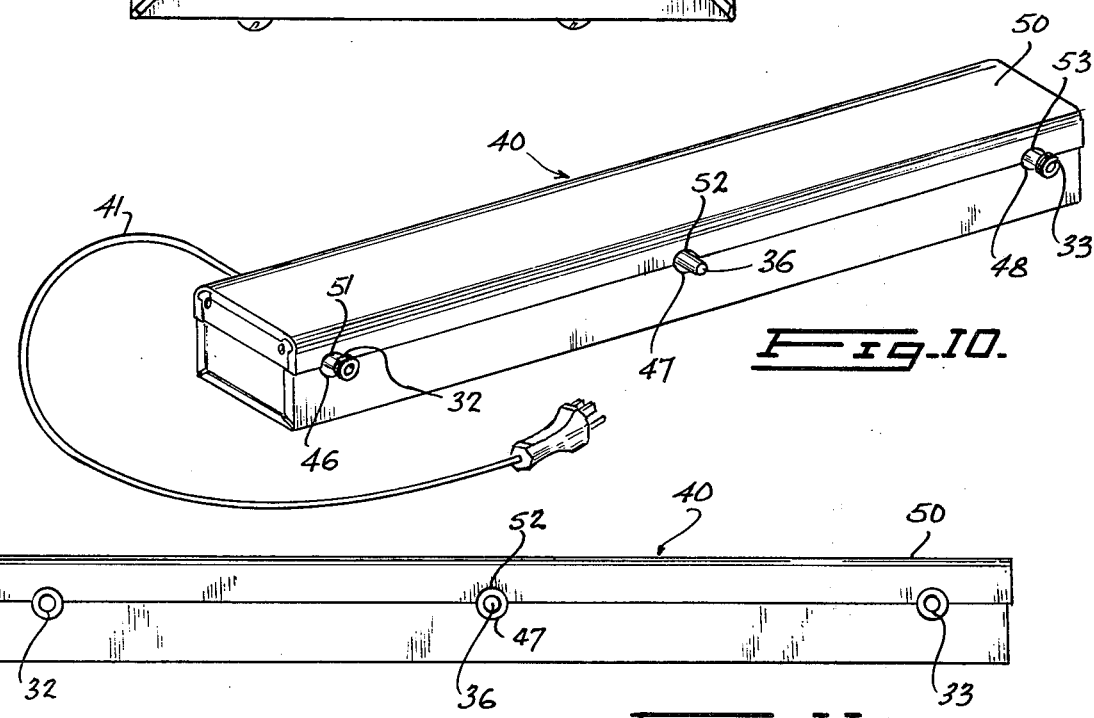
FIG. 10 is a perspective view of a sterilizer assembly incasing a sterilizer unit.
Figure 11:
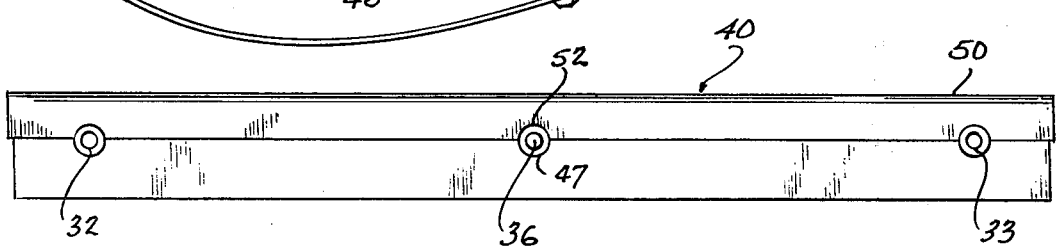
FIG. 11 is a front view of the sterilizer assembly.

As shown in FIG. 6, a sterilizer unit 20 of the kind shown in FIGS. 1 to 4 is placed in the casing 40 with the inlet connection 32, viewport 36 and outlet connection 33 facing up, so that the prongs 34 and 35 are in vertical alignment and fit into a slot 44' in the receptacles 44 and 45, respectively. The unit 20 is then rotated 90° to assume the position shown in FIGS. 6 and 7. The inlet connection 32, viewport 36 and outlet connection 33 fit into the slots 46, 47 and 48, and the prongs are in horizontal alignment and in electrical contact with metallic springs 49, which are in turn connected to terminals located at the bottom of the receptacles 44 and 45. A cover 50 (see FIGS. 10 and 11), having hemispherical slots 51 to 53 complementary to the slots 46 to 48, is then fitted over the casing and fixed thereto by means of screws 54 at each end.

Figure 12:
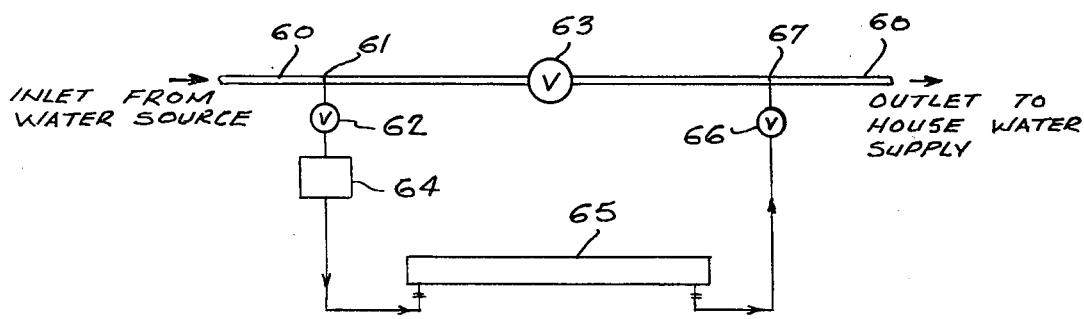
FIG. 12 is a schematic diagram of a water filtering system.

FIG. 12 shows in schematic form a water sterilizing system employing the invention. A water source inlet is connected to a water pipe 60, the water being diverted by means of a connection 61 and valves 62 and 63 through an activated carbon filter 64, and then through a sterilizer assembly 65 according to the invention. By means of a valve 66 and a connection 67 the sterilized water is passed back to the pipe 60 to an outlet leading to the house water supply. It is found to be desirable in practice to locate an activated carbon filter ahead of the sterilizer to remove particles from the water. However, the invention is still required following such filtering to kill bacteria, known to grow in activated carbon filters.

In the embodiment just described, a viewport for visually monitoring the operation of the tube is provided. However, there may be circumstances in which the tube may still generate light but not enough radiation to sterilize the liquid. Accordingly, the embodiments of FIG. 13 and 14 provide for electrically sensing the flow of current through the tube.

Figure 13:
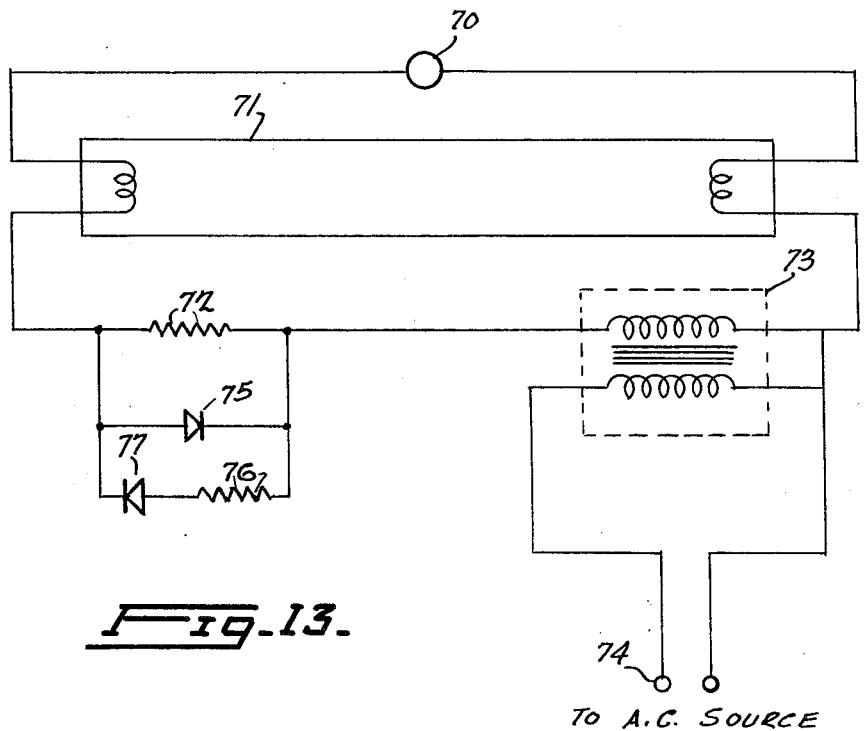
FIG. 13 shows a circuit arrangement for providing a visual means to detect failure of the tube.
Figure 14:
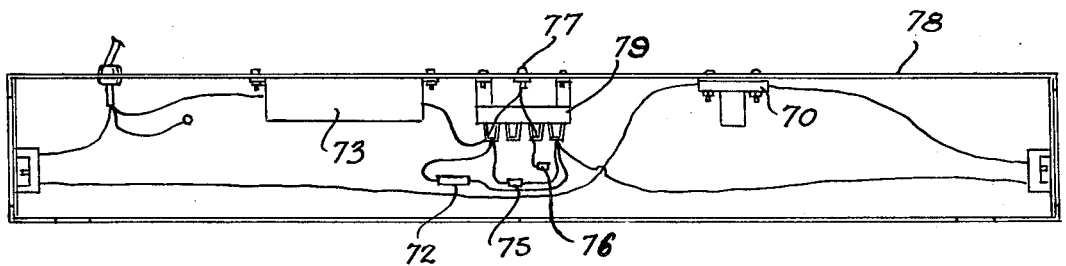
FIG. 14 is a plan view of a case (with cover removed) showing the mounting and connections of the circuit components of FIG. 13.

In FIG. 13, a conventional starter 70 for firing a tube is connected in a circuit with an ultra-violet tube 71, a resistor 72, a conventional ballast 73 and terminals 74 for connection to a conventional source of A.C. voltage. When current flows through the tube 71, a voltage drop is produced across the resistor, with a portion of the current flowing through a diode 75 during the negative half cycle of the A.C. voltage. This current flows through a current limiting resistor 76 and a light emitting diode (LED) 77. The parameters of the circuit are chosen so that as long as there is sufficient current flowing through the tube 71 to sterilize the water, the LED 77 remains on. When there is insufficient current or if the tube 71 is off, the LED also goes off, giving an indication that sterilization is not being achieved.

For G30T8 tube, employing a FS4 starter and a L140FTPC ballast, it has been found that the following circuit components provide satisfactory results:

resistor 72: 10 W 6.8 ohms
diode 75: IN4006
resistor 76: ½ W 27 ohms
LED 77: OL30

Turning to FIG. 14, a casing 78 for housing the tube 71 is provided, including the starter 70, and the ballast 73. A terminal 79 is mounted on the casing for providing interconnections among the circuit components. The LED 77 is mounted to the wall of the casing and protrudes from the exterior thereof so that the light can be readily observed.

If the surfaces of the ultra-violet tube in contact with the water become coated with deposits, the effectiveness of the ultra-violet radiation can be seriously retarded. Thus, some sterilizers are provided with means to prevent the flow of water when sufficient light is being radiated by the tube.

One such arrangement is disclosed in Canadian Pat. No. 674,555 referred to above. The patent uses a photocell that is sensitive to ultra-violet light. The cell is connected in series with a current sensing relay, which in turn operates a valve that opens and closes the water inlet, depending on whether sufficient radiation is being received by the cell from the tube.

Figure 15:
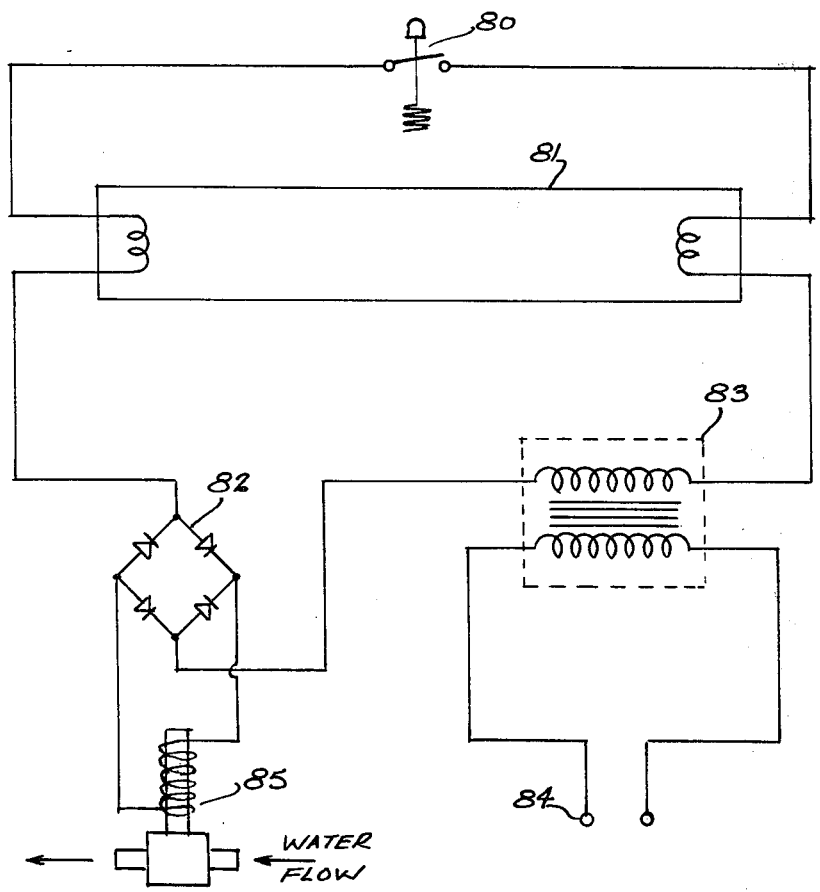
FIG. 15 shows a circuit arrangement for providing a stoppage of water flow upon failure of the tube.
Figure 16:
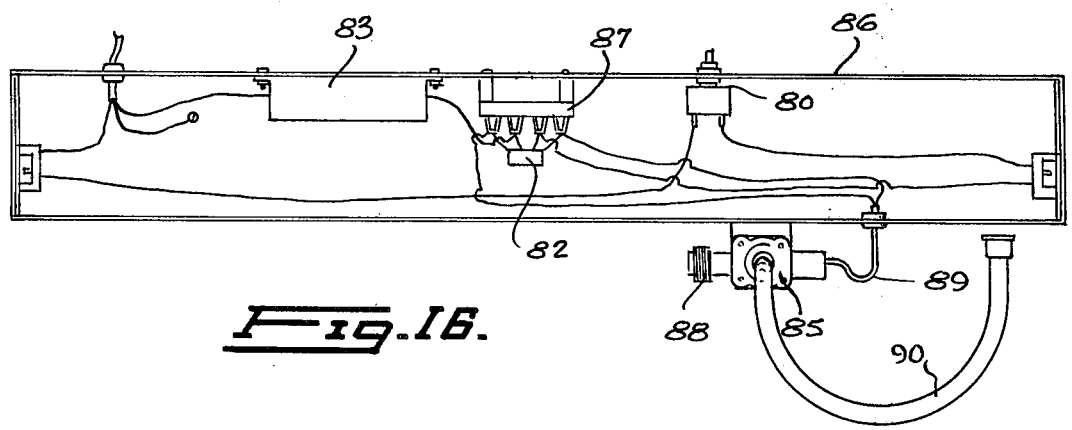
FIG. 16 is a plan view of a case (with cover removed) showing the mounting and connections of the circuit components of FIG. 15.

The embodiment of FIGS. 15 and 16 does not use a photo cell or a relay, but instead directly senses the current flowing through the ultra-violet tube. A normally open spring return push button switch 80 for firing a tube is connected in circuit with an ultra-violet tube 81, a full wave rectifier 82, a conventional ballast 83 and terminals 84 for connection to a conventional source of A.C. voltage. The current flowing through the tube 81 is tapped off by the rectifier 82, with the rectified current flowing through the coil of a solenoid-operated, water control valve 85.

As long as sufficient D.C. current is flowing through the solenoid, the valve remains open, and the water continues to flow through the unit. However, if the current drops due to a failure or defect in the tube 81, the valve closes and the water flow is stopped. If the tube fails for any reason and the valve closes, the sterilizer cannot start again without operating the switch 80.

In FIG. 16, a casing 86 for housing the tube 81 is provided, including the starter 80 having its button protruding from the exterior of the casing and the ballast 83. A terminal 87 is mounted on the casing for providing interconnections and for mounting the rectifier 82. A water inlet 88 is connected to one side of the valve 85, which is mounted to the exterior of the casing 86. The output side of the valve 85 is connected by a short piece of hose 90 through an aperture in the casing (not shown) to the inlet connection of the disposable sterilizer unit. A conduit 89 houses the electrical leads that connect to the solenoid coil.

As will be apparent from the above discussion, sterilizer units fabricated in accordance with the teachings of the invention are within the budget of most home and cottage owners. Moreover, such sterilizer units can be installed without specialized skills, and can be economically throuwn away when worn out or rendered relatively inefficient to residue build-up on the walls of jacket 21 and tube 22 and readily replaced with a new unit at low cost.

Thus, the invention satisfies a need for an inexpensive water sterilizer assembly that is of simple construction, easy to install without special skills, and which advantageously employs a disposable water sterilizer unit. Although the preferred embodiment does not utilize a sheath or a fail-safe device, it is to be understood that such features could readily be added to this embodiment without departing from the spirit and scope of the invention as claimed.

Applicant has also provided sterilizers with mechanisms for sensing the failure of the tube, either by producing a visual indication or by stopping the flow of water to the tube.

While the above provides a full and complete disclosure of the preferred embodiments of the invention, various modifications, alternate constructions and equivalents may be employed without departing from the true spirit and scope of the invention. Therefore the above description and illustrations should not be construed as limiting the scope of the invention which is defined by the appended claims.

What is claimed is:

1. A disposable unit for sterilizing the liquid comprising:
   an elongated plastic jacket having an inner surface and opposing ends,
   an elongated tube for generating radiation to sterilize liquid in said jacket, said tube extending longitudinally along the interior of said jacket and having an outer surface, said inner and outer surface forming a flow chamber within said jacket around said tube, said tube being nonremovably received by said jacket,
   said jacket being substantially opaque to said radiation,
   means adjacent said opposing ends of said jacket for providing an inlet and an outlet for flow of liquid from said inlet into said chamber and into direct contact with said tube for sterilization by the radiation therefrom and finally out of said outlet,
   said jacket ends including liquid tight seals engaging respective ends of said tube to prevent outflow of liquid from said flow chamber except via said outlet,
   said tube ends each terminating in electrically conductive terminal means extending exteriorly of said jacket ends for applying electric power to the tube and for providing mechanical support to said unit.

2. The combination of claim 1 wherein said tube ends each terminates exterior to the associated one of said seals.

3. The combination of claim 1 wherein said tube comprises means for generating ultra-violet radiation having a wavelength of substantially 2,537 Angstroms.

4. The combination of claim 1 wherein said tube comprises means for generating radiation having a wavelength of substantially 1,880 Angstroms.

5. A combination of claim 1 wherein said jacket is provided with a view port exposed to said radiation.

6. The combination of claim 1 wherein said means for providing an inlet and an outlet comprises a spaced pair of externally threaded projecting members each adapted to be coupled to an internally threaded hose connection and each provided with a central through bore.

7. The combination of claim 1 wherein each of said ends of said jacket is provided with an integrally molded closure member; and
   wherein said means for providing an inlet and an outlet comprises first and second connection portions each integrally formed to a different one of said closure members, each connection portion having a central opening communicting with said chamber.

8. The combination of claim 7 wherein at least one of said closure members includes fin means internal thereto for imparting turbulence to said liquid flowing therepast.

9. The combination of claim 7 wherein each of said seals comprises an O-ring engaged with the inner wall surface of the associated closure member.

10. The combination of claim 1 further including means for restricting the flow rate of said liquid through said chamber to a predetermined maximum value.

11. The combination of claim 10 wherein said restricting means comprises means for limiting said flow rate to four gallons per minute.

12. The combination of claim 1 further including an elongated casing for mounting said disposable unit, said casing having fixedly mounted therein spaced apart mounting means for receiving respective ones of said terminal means for thereby locating said unit in said casing,
   said mounting means including electric contact means for engaging said terminal means for connecting an external source of power to said terminal means to energize said tube.

13. The combination of claim 12 wherein said terminal means at each tube end comprises a pair of parallel prongs defining a first plane, and wherein each said mounting means in said casing includes socket means for receiving said prongs, said socket means comprising a first socket portion defining a second plane for enabling said prongs to enter said first portion by alignment of said first and second planes, said socket means further comprising arcuate socket portions extending around and communicating with said first socket portion to enable said prongs to enter said arcuate socket portions upon rotation of said unit in order to locate and retain said unit in said socket means, said electric contact means being located in said arcuate socket portions whereby upon said rotation said terminal means are connected to an external source of power.

* * * * *